(12) United States Patent
Buevich et al.

(10) Patent No.: US 9,848,955 B2
(45) Date of Patent: *Dec. 26, 2017

(54) RESORBABLE POUCHES FOR IMPLANTABLE MEDICAL DEVICES

(71) Applicant: TYRX Inc., Monmouth Junction, NJ (US)

(72) Inventors: Fatima Buevich, Highland Park, NJ (US); Arikha Moses, New York, NY (US); Frank Do, Jersey City, NJ (US); William McJames, Bellemeade, NJ (US); William Edelman, Sharon, MA (US); Mason Diamond, Wayne, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 168 days.

This patent is subject to a terminal disclaimer.

(21) Appl. No.: 14/643,182

(22) Filed: Mar. 10, 2015

(65) Prior Publication Data

US 2015/0238262 A1   Aug. 27, 2015

Related U.S. Application Data

(62) Division of application No. 11/936,051, filed on Nov. 6, 2007, now Pat. No. 9,023,114.

(Continued)

(51) Int. Cl.
*A61B 50/30* (2016.01)
*A61K 31/195* (2006.01)
(Continued)

(52) U.S. Cl.
CPC ............ *A61B 50/30* (2016.02); *A61K 31/195* (2013.01); *A61K 31/445* (2013.01);
(Continued)

(58) Field of Classification Search
CPC .............. A61B 50/30; A61B 2050/314; A61B 2017/00004; A61L 31/04; A61L 31/16; A61L 31/148
See application file for complete search history.

(56) References Cited

U.S. PATENT DOCUMENTS 4,298,997 A   11/1981   Rybka
4,326,532 A   4/1982   Hammar
(Continued)

FOREIGN PATENT DOCUMENTS

EP   0971753 B1   10/2005
JP   07-000430 A   1/1995
(Continued)

OTHER PUBLICATIONS

Australian Patent Examination Report No. 2 dated Apr. 14, 2016; Australian Divisional Patent Application No. 2013200627; Title: Resorbable Pouches for Implantable Medical Devices.
(Continued)

*Primary Examiner* — Bradley Osinski
(74) *Attorney, Agent, or Firm* — Sorell Lenna & Schmidt, LLP

(57) ABSTRACT

Biodegradable and resorbable polymer pouches are described for use with cardiac rhythm management devices (CRMs) and other implantable medical devices (IMDs), i.e., a pouch, covering, or other receptacle capable of encasing, surrounding and/or holding the CRM or other IMD for the purpose of securing it in position, inhibiting or reducing bacterial growth, providing pain relief and/or inhibiting scarring or fibrosis on or around the CRM or other IMD. Optionally, the biodegradable and resorbable pouches of the invention include one or more drugs in the polymer matrix
(Continued)

to provide prophylactic effects and alleviate side effects or complications associated with the surgery or implantation of the CRM or other IMD.

20 Claims, 4 Drawing Sheets

Related U.S. Application Data

(60) Provisional application No. 60/984,254, filed on Oct. 31, 2007, provisional application No. 60/864,597, filed on Nov. 6, 2006.

(51) Int. Cl.
*A61K 31/445* (2006.01)
*A61K 31/496* (2006.01)
*A61L 31/14* (2006.01)
*A61L 31/16* (2006.01)
*A61L 31/04* (2006.01)
*A61B 17/00* (2006.01)
*A61N 1/375* (2006.01)
*A61B 90/00* (2016.01)

(52) U.S. Cl.
CPC ............ *A61K 31/496* (2013.01); *A61L 31/04* (2013.01); *A61L 31/148* (2013.01); *A61L 31/16* (2013.01); *A61B 2017/00004* (2013.01); *A61B 2017/00889* (2013.01); *A61B 2017/00893* (2013.01); *A61B 2050/314* (2016.02); *A61B 2090/0815* (2016.02); *A61L 2300/00* (2013.01); *A61L 2300/45* (2013.01); *A61L 2400/18* (2013.01); *A61N 1/375* (2013.01)

(56) References Cited

U.S. PATENT DOCUMENTS

| | | |
|---|---|---|
| 4,642,104 A | 2/1987 | Sakamoto et al. |
| 4,713,073 A | 12/1987 | Reinmuller |
| 4,769,038 A | 9/1988 | Bendavid |
| 4,846,844 A | 7/1989 | De Leon et al. |
| 4,980,449 A | 12/1990 | Kohn et al. |
| 5,099,060 A | 3/1992 | Kohn et al. |
| 5,216,115 A | 6/1993 | Kohn et al. |
| 5,217,493 A | 6/1993 | Raad et al. |
| 5,279,594 A | 1/1994 | Jackson |
| 5,295,978 A | 3/1994 | Fan et al. |
| 5,317,077 A | 5/1994 | Kohn et al. |
| 5,362,754 A | 11/1994 | Raad |
| 5,417,671 A | 5/1995 | Jackson |
| 5,512,055 A | 4/1996 | Domb et al. |
| 5,554,147 A | 9/1996 | Batich |
| 5,587,507 A | 12/1996 | Kohn et al. |
| 5,607,417 A | 3/1997 | Batich |
| 5,607,477 A | 3/1997 | Schindler et al. |
| 5,614,284 A | 3/1997 | Kranzler et al. |
| 5,624,704 A | 4/1997 | Darouiche et al. |
| 5,658,995 A | 8/1997 | Kohn et al. |
| 5,670,602 A | 9/1997 | Kohn et al. |
| 5,676,146 A | 10/1997 | Scarborough |
| 5,722,992 A | 3/1998 | Goldmann |
| 5,755,758 A | 5/1998 | Woloszko |
| 5,756,145 A | 5/1998 | Darouiche |
| 5,810,786 A | 9/1998 | Jackson |
| 5,834,051 A | 11/1998 | Woloszko |
| 5,853,745 A | 12/1998 | Darouiche |
| 5,902,283 A | 5/1999 | Darouiche et al. |
| 5,912,225 A * | 6/1999 | Mao ............ A61K 9/204 514/1.3 |
| 6,013,853 A | 1/2000 | Athanasiou |
| 6,048,521 A | 4/2000 | Kohn et al. |
| 6,096,070 A | 8/2000 | Ragheb |
| 6,099,562 A | 8/2000 | Ding |
| 6,103,255 A | 8/2000 | Levene et al. |
| 6,120,491 A | 9/2000 | Kohn et al. |
| 6,162,487 A | 12/2000 | Darouiche |
| RE37,160 E | 5/2001 | Kohn et al. |
| 6,267,772 B1 | 7/2001 | Mulhauser et al. |
| 6,306,176 B1 | 10/2001 | Whitbourne |
| 6,319,264 B1 | 11/2001 | Tormala |
| 6,319,492 B1 | 11/2001 | Kohn et al. |
| 6,335,029 B1 | 1/2002 | Kamath |
| 6,337,198 B1 | 1/2002 | Levene et al. |
| RE37,795 E | 7/2002 | Kohn et al. |
| 6,461,644 B1 | 10/2002 | Jackson |
| 6,475,434 B1 | 11/2002 | Darouiche |
| 6,475,477 B1 | 11/2002 | Kohn et al. |
| 6,514,286 B1 | 2/2003 | Leatherbury |
| 6,548,569 B1 | 4/2003 | Williams et al. |
| 6,558,686 B1 | 5/2003 | Darouiche |
| 6,584,363 B2 | 6/2003 | Heil |
| 6,589,546 B2 | 7/2003 | Kamath |
| 6,589,591 B1 | 7/2003 | Mansouri |
| 6,602,497 B1 | 8/2003 | Kohn et al. |
| 6,656,488 B2 | 12/2003 | Yi et al. |
| 6,719,987 B2 | 4/2004 | Langford et al. |
| 6,719,991 B2 | 4/2004 | Darouiche et al. |
| 6,753,071 B1 | 6/2004 | Pacetti |
| 6,838,493 B2 | 1/2005 | Williams et al. |
| 6,852,308 B2 | 2/2005 | Kohn et al. |
| 6,887,270 B2 | 5/2005 | Miller |
| 6,916,483 B2 | 7/2005 | Ralph |
| 6,916,868 B2 | 7/2005 | Kemnitzer |
| 6,961,610 B2 | 11/2005 | Yang |
| 6,968,234 B2 | 11/2005 | Stokes |
| 6,981,944 B2 | 1/2006 | Jamiolkowski et al. |
| 6,986,899 B2 | 1/2006 | Hossainy |
| 6,991,802 B1 | 1/2006 | Ahola |
| 7,005,454 B2 | 2/2006 | Brocchini |
| 7,056,493 B2 | 6/2006 | Kohn et al. |
| 7,195,615 B2 | 3/2007 | Tan |
| 7,250,154 B2 | 7/2007 | Kohn et al. |
| 7,271,234 B2 | 9/2007 | Kohn et al. |
| 7,326,425 B2 | 2/2008 | Kohn et al. |
| 8,315,700 B2 | 11/2012 | Citron et al. |
| 2002/0072694 A1 | 6/2002 | Snitkin et al. |
| 2002/0151668 A1 | 10/2002 | James et al. |
| 2003/0091609 A1 | 5/2003 | Hendriks |
| 2003/0138488 A1 | 7/2003 | Kohn et al. |
| 2003/0175410 A1 | 9/2003 | Campbell et al. |
| 2003/0216307 A1 | 11/2003 | Kohn et al. |
| 2003/0224033 A1 | 12/2003 | Li |
| 2004/0010276 A1 | 1/2004 | Jacobs et al. |
| 2004/0146546 A1 | 7/2004 | Gravett |
| 2004/0147688 A1 | 7/2004 | Kemnitzer et al. |
| 2004/0172048 A1 | 9/2004 | Browning |
| 2004/0186528 A1 | 9/2004 | Ries |
| 2004/0186529 A1 | 9/2004 | Bardy et al. |
| 2004/0209538 A1 | 10/2004 | Klinge et al. |
| 2004/0220249 A1 | 11/2004 | Puder et al. |
| 2004/0220665 A1 | 11/2004 | Hossainy |
| 2004/0245671 A1 | 12/2004 | Smit |
| 2004/0253293 A1 | 12/2004 | Shafiee |
| 2004/0254334 A1 | 12/2004 | James et al. |
| 2005/0008671 A1 | 1/2005 | Van Antwerp |
| 2005/0015102 A1 | 1/2005 | Chefitz |
| 2005/0031669 A1 | 2/2005 | Shafiee |
| 2005/0033132 A1* | 2/2005 | Shults ............... A61B 5/14532 600/347 |
| 2005/0101692 A1 | 5/2005 | Sohier et al. |
| 2005/0112171 A1 | 5/2005 | Tang |
| 2005/0113849 A1 | 5/2005 | Popadiuk |
| 2005/0118227 A1 | 6/2005 | Kohn et al. |
| 2005/0147690 A1 | 7/2005 | Masters et al. |
| 2005/0149157 A1 | 7/2005 | Hunter et al. |
| 2005/0163821 A1 | 7/2005 | Sung et al. |
| 2005/0165203 A1* | 7/2005 | Kohn .................. A61K 9/0024 528/176 |
| 2005/0169959 A1 | 8/2005 | Hunter |
| 2005/0208095 A1 | 9/2005 | Hunter et al. |

(56) References Cited

U.S. PATENT DOCUMENTS

| | | | |
|---|---|---|---|
| 2005/0208664 A1 | 9/2005 | Keegan et al. | |
| 2005/0209664 A1 | 9/2005 | Hunter et al. | |
| 2005/0228471 A1 | 10/2005 | Williams et al. | |
| 2005/0233062 A1 | 10/2005 | Hossainy | |
| 2005/0245637 A1 | 11/2005 | Hossainy | |
| 2005/0267543 A1* | 12/2005 | Heruth | A61N 1/375 607/36 |
| 2006/0009806 A1 | 1/2006 | Heruth | |
| 2006/0025852 A1 | 2/2006 | Armstrong et al. | |
| 2006/0034769 A1 | 2/2006 | Kohn et al. | |
| 2006/0035854 A1 | 2/2006 | Goldstein et al. | |
| 2006/0062825 A1 | 3/2006 | Maccecchini | |
| 2006/0067908 A1 | 3/2006 | Ding | |
| 2006/0073182 A1 | 4/2006 | Wong | |
| 2006/0095134 A1 | 5/2006 | Trieu | |
| 2006/0115449 A1 | 6/2006 | Pacetti | |
| 2006/0121179 A1 | 6/2006 | Pacetti | |
| 2006/0134168 A1 | 6/2006 | Chappa | |
| 2006/0142786 A1 | 6/2006 | Mathisen | |
| 2006/0204440 A1 | 9/2006 | Kohn et al. | |
| 2006/0246103 A1 | 11/2006 | Ralph et al. | |
| 2007/0196421 A1 | 8/2007 | Hunter et al. | |
| 2007/0198040 A1 | 8/2007 | Buevich et al. | |
| 2007/0299155 A1 | 12/2007 | Carpenter et al. | |
| 2008/0107709 A1 | 5/2008 | Kohn et al. | |
| 2008/0132922 A1 | 6/2008 | Buevich et al. | |
| 2008/0241212 A1 | 10/2008 | Moses et al. | |
| 2009/0018559 A1 | 1/2009 | Buevich et al. | |
| 2009/0029961 A1 | 1/2009 | Modak et al. | |
| 2009/0088548 A1 | 4/2009 | Moses et al. | |
| 2009/0149568 A1 | 6/2009 | Pacetti | |
| 2010/0015237 A1 | 1/2010 | Moses et al. | |
| 2010/0074940 A1 | 3/2010 | Schwartz et al. | |
| 2010/0129417 A1 | 5/2010 | Moses et al. | |
| 2010/0130478 A1 | 5/2010 | Moses et al. | |
| 2010/0167992 A1 | 7/2010 | Schwartz et al. | |
| 2010/0168808 A1 | 7/2010 | Citron | |

FOREIGN PATENT DOCUMENTS

| | | |
|---|---|---|
| JP | 2000-512519 A | 9/2000 |
| JP | 2002-500065 A | 1/2002 |
| JP | 2002-522112 A | 7/2002 |
| JP | 2004-524059 A | 8/2004 |
| JP | 2004-535866 A | 12/2004 |
| JP | 2005-152651 A | 6/2005 |
| JP | 2007500552 A | 1/2007 |
| WO | WO9508305 | 3/1995 |
| WO | 9747254 A1 | 12/1997 |
| WO | WO9832474 | 7/1998 |
| WO | 9924107 A1 | 5/1999 |
| WO | WO9924107 | 5/1999 |
| WO | 9934750 A1 | 7/1999 |
| WO | WO 99/52962 | 10/1999 |
| WO | WO 01/49249 | 7/2001 |
| WO | WO 01/49311 | 7/2001 |
| WO | WO 03/091337 | 11/2003 |
| WO | 2004071485 A1 | 8/2004 |
| WO | 2005/011767 A1 | 2/2005 |
| WO | WO2005055972 | 6/2005 |
| WO | 2005061003 A1 | 7/2005 |
| WO | 2006133569 A1 | 12/2006 |
| WO | 2007056134 A2 | 5/2007 |
| WO | WO2007056134 | 5/2007 |
| WO | WO 2008/127411 | 10/2008 |
| WO | 2008137807 A1 | 11/2008 |
| WO | WO 2008/136856 | 11/2008 |
| WO | WO 2008/121816 | 12/2008 |
| WO | 2009/113972 A2 | 9/2009 |
| WO | WO 2009/113972 | 9/2009 |
| WO | 2010006046 A1 | 1/2010 |
| WO | 2010141475 A1 | 12/2010 |

OTHER PUBLICATIONS

International Search Report and Written Opinion for Application No. PCT/US2011/049140 dated Aug. 27, 2012.
International Search Report and Written Opinion, PCT/US11/60197, dated Mar. 2, 2012.
Canadian Office Action for Application No. 2,667,867 dated Aug. 19, 2013, Oct. 17, 2016.
New product introduction at Tyrx Pharma, Inc. The Journal of Product and Brand management, US, Dec. 1, 2006, p. 468-472 The publication date has been recognized based on the description in http://www.ingentaconnect.com/content/mcb/096/2006/00000015/00000007/art00008, "Publication date: Dec. 1, 2006"[Date of SearchApr. 16, 2012].
Japanese Office Action for Application No. 2009-535509 dated Apr. 15, 2013.
Parsonnet, Pacing and Clinical Electrophysiology, 17, 1994.
Enhancing Medical Devices, Sep. 2005, <URL: http://www.tyrx.com/Collateral/documents/TyRx%20English-US/03-06-pr.pdf>.
Japanese Office Action for Application No. 2010-502992 dated Apr. 17, 2013.
Canadian Office Action for Application No. CA/2667873 dated Feb. 11, 2013.
Japanese Office Action for Application No. 2009-535508 dated Aug. 14, 2012.
Extended European Search Report for Application No. 07873600 dated Aug. 30, 2012.
Extended European Search Report for Application No. EP07874257 dated Aug. 29, 2012.
Australian Examination Report for Application No. 2007344645 dated Mar. 8, 2012.
TYRX Pharma, Inc. Announces Submission of a Premarket Application for PIVIT CRM, TYRX Press Releases [searched on Apr. 16, 2012], USA, Oct. 16, 2006, URL, http://www.tyrx.com/Collateral/Documents/TyRx%20English-US/10-16-06-pr.pdf.
TyRx Pharama, Inc., TyRx Press Releases, TyRx Announces FDA 510(k) Filing for New Surgical Mesh, USA, May 17, 2005, [searched on May 2, 2012], URL, http://www.tyrx.com/Collateral/Documents/TyRx%20English-US/10-17-05-pr.pdf.
TyRx Pharama, Inc., TyRx Press Releases, TyRx Pharama's Anesthetic Coated Surgical Mesh Combination Product Assigned to "Device" Center at FDA, USA, Jan. 9, 2006, [searched on May 2, 2012], URL, http://www.tyrx.com/Collateral/Documents/TyRx%20English-US/01-09-06-pr.pdf.
TyRx Pharama, Inc., TyRx Press Releases, TyRx Announces FDA 510(k) Filing for New Antibiotic Eluting Surgical Mesh, USA, Jan. 17, 2006, [searched on May 2, 2012] URL, http://www.tyrx.com/Collateral/Documents/TyRx%20English-US/01-17-06-pr.pdf.
Zoll, Annals of Surgery, Sep. 1964.
Areolar Tissue, The Free Dictionary, May 2011.
Rupp, Clinical Infectious Diseases, vol. 19, 1994.
Darouiche, NEJM, 340, 1999.
Green, Clinical Cornerstone, vol. 3, 2001.
Agostinho, A. et al., "Inhibition of Staphylococcus aureus Biofilms by a Novel Antibacterial Envelope for Use with Implantable Cardiac Devices," Clinical and Translational Science, 2009, vol. 2(3), pp. 193-198.
Ajmal, N. et al., "The Effectiveness of Sodium 2-Mercaptoethane Sulfonate (Mesna) in Reducing Capsular Formation around Implants in a Rabbit Model," 2003, Plastic and Reconstructive Surgery, vol. 112(5), pp. 1455-1461.
Bach, A. et al., "Retention of antibacterial activity and bacterial colonization of antiseptic-bonded central venous catheters," J. Antimicrob. Chemother., 1996, vol. 37(2), pp. 315-322.
Collin, G. R., "Decreasing catheter colonization through the use of an antiseptic-impregnated catheter: a continuous quality improvement project," Chest., 1999, vol. 115(6), pp. 1632-1640.
Darouiche, R. O. et al., "A comparison of two antimicrobial-impregnated central venous cathethers," The New England Journal of Medicine, 1999, vol. 340(1), pp. 1-8.
Darouiche, R. O. et al., "Efficacy of antimicrobial-impregnated silicone sections from penile implants in preventing device colonization in an animal model," Urology, 2002, vol. 59, pp. 303-307.

(56) References Cited

OTHER PUBLICATIONS

Darouiche, R. O. et al., "In vivo efficacy of antimicrobe-impregnated saline-filled silicone implants," Plast. Reconstr. Surg., 2002, vol. 109(4), pp. 1352-1357.
Engelmayr, G. C., Jr. et al., "A novel bioreactor for the dynamic flexural stimulation of tissue engineered heart valve biomaterials," Biomaterials, 2003, vol. 24, pp. 2523-2532.
George, S. J. et al., "Antiseptic-impregnated central venous catheters reduce the incidence of bacterial colonization and associated infection in immunocompromised transplant patients," Eur. J. Anaesthesiol., 1997, vol. 14, pp. 428-431.
Greca, F. H. et al., "The influence of differing pore sizes on the biocompatibility of two polypropylene meshes in the repair of abdominal defects," Hernia, 2001, vol. 5, pp. 59-64.
Hambraeus, A. et al., "Bacterial contamination in a modern operating suite, 2. Effect of a zoning system on contamination of floors and other surfaces," J. Hyg., 1978, vol. 80, pp. 57-67.
Hayes, B. B. et al., "Evaluation of percutaneous penetration of natural rubber latex proteins," Toxicol. Sci., 2000, vol. 56, pp. 262-270.
Hospital Infections Program, National Center for Infectious Disease, CDC, "Public Health Focus: Surveillance, Prevention, and Control of Nosocomial Infections," MMWR Weekly, 1992, vol. 41, pp. 783-787.
Khodorova, A. B. et al., "The addition of dilute epinephrine produces equieffectiveness of bupivacaine enantiomers for cutaneous analgesia in the rat," Anesth. Analg., 2000, vol. 91, pp. 410-416.
Kramer, C. et al., "A fatal overdose of transdermally administered fentanyl," J. Am. Osteopath. Assoc., 1998, vol. 98(7), pp. 385-386.
Lau, H. et al,. "Randomized clinical trial of postoperative subfascial infusion with bupivacaine following ambulatory open mesh repair of inguinal hernia," Dig. Surg., 2003, vol. 20(4), pp. 285-289.
Leblanc, K. A., et al., "Evaluation of continuous infusion of 0.5% bupivacaine by elastomeric pump for postoperative pain management following open inguinal hernia repair," J. Am. Coll. Surg., 2005, vol. 200(2), pp. 198-202.
Li, H. et al., "Antibacterial activity of antibiotic coated silicon grafts," J. Urol., 1998, vol. 160(5), pp. 1910-1913.
Maki, D. G. et al., "Engineering out the risk of infection with urinary catheters," Emerging Infectious Diseases, 2001, vol. 7(2), pp. 342-347.
Maki, D. G. et al., "Prevention of central venous catheter-related bloodstream infection by use of an antiseptic-impregnated catheter: A randomized, controlled trial," Annals of Internal Medicine, 1997, vol. 127(4), pp. 257-266.
Meakins, J. L., "Prevention of postoperative infection," ACS Surgery: Principals and Practice, American College of Surgeons, 2005, pp. 1-20.
Morrow, T. J. et al, "Suppression of bulboreticular unit responses to noxious stimuli by analgesic mesencephalic stimulation," Somatosensory Research, 1983, vol. 1(2), pp. 151-168.
Pearson, M. L., et al., "Reducing the risk for catheter-related infections: A new strategy," Ann. Intern. Med., 1997, vol. 127(4), pp. 304-306.
Perencevich, E. N. et.al., "Health and economic impact of surgical site infections diagnosed after hospital discharge," Emerging Infect. Dis., 2003, vol. 9(2), pp. 196-203.
Raad, I. et al., "Central venous catheters coated with minocycline and rifampin for the prevention of catheter-related colonization and bloodstream infections: A randomized, double-blind trial," Ann. Intern. Med., 1997, vol. 127(4), pp. 267-274.
Sanchez, B. et al., "Local anesthetic infusion pumps improve postoperative pain after inguinal hernia repair," The American Surgeon, 2004, vol. 70, pp. 1002-1006.
Segura, M. et al., "A clinical trial on the prevention of catheter-related sepsis using a new hub model," Ann. Surg., 1996, vol. 223(4), pp. 363-369.
Tennenberg, S. et al., "A prospective randomized trial of an antibiotic- and antiseptic-coated central venous catheter in the prevention of catheter-related infections," Arch. Surg., 1997, vol. 132, pp. 1348-1351.
van't Riet, M. et al, "Prevention of adhesion to prosthetic mesh: Comparison of different barriers using an incisional hernia model," Annals of Surgery, 2003, vol. 237, No. 1, pp. 123-128.
Final Office Action for U.S. Appl. No. 11/672,929, dated Aug. 16, 2010, 19 pages.
Final Office Action for U.S. Appl. No. 11/936,049, dated Dec. 21, 2010, 20 pages.
Final Office Action for U.S. Appl. No. 12/058,060, dated Oct. 13, 2010, 19 pages.
Yourassowsky, E. et al., "Combination of Minocycline and Rifampicin against Methicillin- and Gentamicin-Resistant *Staphylococcus aureus*," J. Clin. Pathol., 1981, pp. 559-563, vol. 34.
Clumeck, N. et al., "Treatment of Severe *Staphylococcal* Infections with a Rifampicin-Minocycline Association," J. Antimicrob. Chemother., 1984, pp. 17-22, vol. 13(SuppC).
Zinner, S. H. et al., "Antistaphylococcal Activity of Rifampin with Other Antibiotics," J. Infect. Dis., Oct. 1981, pp. 365-371, vol. 144(4).
Kohn, J., "Implants: The Biodegradable Future," Mar. 1, 2006, <URL: http://www.medicaldevice-network.com/features/feature_168/>.
van't Riet, M. et al., "Prevention of Adhesion Formation to Polypropylene Mesh by Collagen Coating," Surg. Endosc., 2004, pp. 681-685, vol. 18.
Office Action for U.S. Appl. No. 11/672,929, dated Feb. 3, 2010, 11 pages.
Office Action for U.S. Appl. No. 12/058,060, dated Jan. 22, 2010, 10 pages.
Office Action for U.S. Appl. No. 11/936,049, dated Apr. 14, 2010, 18 pages.
International Search Report and Written Opinion for International Application No. PCT/US2008/058652, dated Sep. 12, 2008, 7 pages.
International Preliminary Report on Patentability for International Application No. PCT/US2008/058652, dated Sep. 29, 2009, 5 pages.
International Search Report and Written Opinion for International Application No. PCT/US2007/083843, dated Sep. 11, 2008, 7 pages.
International Preliminary Report on Patentability for International Application No. PCT/US2007/083843, dated May 12, 2009, 7 pages.
International Preliminary Report on Patentability for International application PCT/US2007/083841.
International Search Report from PCT/US07/83841, dated Oct. 31, 2008, 3 pp.
Written Opinion from PCT/US07/83841, dated Oct. 31, 2008, 5 pp.
Baddour et al., 2003, "Nonvalvular cardiovascular device-related infections," Circulation 108:2015-2031.
Chamis et al., 2001, "*Staphylococcus aureus* bateremia in patients with permanent pacemakers of implantable cardioverter-defibrillators," Circulation 104:1029-1033.
Da Costa et al., 1998, "Antibiotic prophylaxis for permanent pacemaker implantation: a meta-analysis," Circulation 97:1796-1801.
Cabell et al., 2004, "Increasing rates of cardiac device infections among Medicare beneficiaries: 1990-1999," American Heart Journal 147(4):582-586.
Costerton et al., 2003, "The application of biofilm science to the study and control of chronic bacterial infections," J. Clin. Investigation 112(10):1466-1477.
Darouiche, 2003, "Antimicrobial approaches for preventing infections associated with surgical implants," Clin. Infect. Dis. 36:1284-1289.
Darouiche, 2004, "Treatment of infections associated with surgical implants," NEJM 350:1422-1429.
Donlan, 2001, "Biofilms and device-associated infections," Emerg. Infect. Dis. 7:277-281.

(56) References Cited

OTHER PUBLICATIONS

Falagas et al., 2007, "Rifampicin-impregnated central venous catheters: a meta-analysis of randomized controlled trials," J. Antimicrob. Chemother. 59:359-369.

Sohail et al., 2007, "Management and outcome of permanent pacemaker and implantable cardioverter-defibrillator infections," J. American College of Cardiology 49:1851-1859.

Wilkoff, 2007, "How to treat and identify device infections," Heart Rhythm 4:1467-1470.

* cited by examiner

Top View

Bottom View

Side View

RESORBABLE POUCHES FOR IMPLANTABLE MEDICAL DEVICES

This application is a divisional of U.S. patent application Ser. No. 11/936,051, filed on Nov. 6, 2006, which claims priority under 35 U.S.C. §119(e)(5) to U.S. Provisional Patent Application No. 60/984,254, filed Oct. 31, 2007 and to U.S. Provisional Patent Application No. 60/864,597, filed Nov. 6, 2006 Each of these applications is incorporated herein by reference, in their entireties.

FIELD OF THE INVENTION

Biodegradable and resorbable polymer pouches are described for use with cardiac rhythm management devices (CRMs) and other implantable medical devices (IMDs), i.e., a pouch, covering, or other receptacle capable of encasing, surrounding and/or holding the CRM or other IMD for the purpose of securing it in position, inhibiting or reducing bacterial growth, providing pain relief and/or inhibiting scarring or fibrosis on or around the CRM or other IMD. Optionally, the biodegradable and resorbable pouches of the invention include one or more drugs in the polymer matrix to provide prophylactic effects and alleviate side effects or complications associated with the surgery or implantation of the CRM or other IMD.

BACKGROUND OF THE INVENTION

In 1992, it was reported that nosocomial infections involved over 2 million patients each year and cost the healthcare systems over 4.5 billion dollars annually.[1] Today, these numbers are undoubtedly much higher. Surgical site infections, involving approximately 500,000 patients, represent the second most common cause of nosocomial infections and approximately 17% of all hospital-acquired infections.[2] The incidence of infections associated with the placement of pacemakers has been reported as 0.13 to 19.9% at an average cost of $35,000 to treat these complications which most often involves complete removal of the implant.[3,4]

Post-operative infection is tied to three elements: lack of host defense mechanisms, surgical site and bacteria present at the time of device implantation.[5] The general health of the patient (i.e., the host factor) is always important; however, since many patients requiring surgery are compromised in some way—and there is little that can be done to mitigate that factor—controlling the other two factors becomes important.

Studies have shown that patients are exposed to bacterial contamination in the hospital, especially in the operating room (OR) and along the route to the OR.[6] In fact, bacterial counts of up to $7.0 \times 10^4$ $CFU/m^2$ have been found in the OR dressing area.[6] Recent improvements in air handling and surface cleansing have reduced the environmental levels of infectious agents, but not eliminated them. Consequently, further means to reduce bacterial contamination or to reduce the potential for bacterial infection are desirable.

Controlling the inoculation levels is the third component to the intra- and post-operative surgical infection control triad. One aspect to microbial control is the use antibiotics. For example, one practice advocates the administration of systemic antibiotics within 60 minutes prior to incision, with additional dosing if the surgery exceeds 3 hours.[5] Such pre-incision administration has shown some positive effects on the incidence of infection associated with the placement of pacemakers.[7] An adjunctive approach to managing the potential for implant contamination has been the introduction of antimicrobial agents on IMDs.[8,9]

This approach was initially developed to create a barrier to microbial entry into the body via surface-penetrating devices, such as indwelling catheters,[9-11] The antimicrobial agents were applied in solution as a direct coating on the device to prevent or reduce bacterial colonization of the device and, therefore, reduce the potential for a device-related infection. While several clinical trials with antimicrobial coatings on device surfaces, such as central venous catheters, show reduced device colonization and a trend towards reduction of patient infection, the results have not been statistically significant.[12-18] Nevertheless, these results are highly relevant since they tend to establish that, with proper aseptic and surgical techniques as well as administration of appropriate antibiotic therapy, the use of surface-modified devices does have a positive impact on the overall procedural/patient outcome.[12,13]

The development of post-operative infection is dependent on many factors, and it is not clear exactly how many colony forming units (CFUs) are required to produce clinical infection. It has been reported that an inoculation $10^3$ bacteria at the surgical site produces a wound infection rate of 20%.[5] And while current air-handling technology and infection-control procedures have undoubtedly reduced the microbial levels in the hospital setting, microbial contamination of an implantable device is still possible. It is known that bacteria, such as *Staphylococcus* can produce bacteremia within a short time after implantation (i.e., within 90 days) with a device or lay dormant for months before producing an active infection so eradication of the bacterial inoculum at the time of implantation is key and may help to reduce late-stage as well as early-stage device-related infections.[22]

For example, the combination of rifampin and minocycline has demonstrated antimicrobial effectiveness as a coating for catheters and other implanted devices, including use of those drugs in a non-resorbable coating such as silicone and polyurethane.[13,19-21] The combination of rifampin and minocycline has also been shown to reduce the incidence of clinical infection when used as a prophylactic coating on penile implants. Additionally, U.S. Ser. No. 60/771,827, filed Feb. 8, 2006 and its related cases, describe bioresorbable polymer coating on a surgical mesh as a carrier for the antimicrobial agents (rifampin and minocycline).

The addition of the antimicrobial agents permits the pouch to deliver antimicrobial agents to the implant site and thus to provide a barrier to microbial colonization of the CRM or other IMD during surgical implantation as an adjunct to surgical and systemic infection control.

A fully resorbable pouch has advantages over non-resorbable meshes which, for example, can become encased with or embedded in dense fibrous tissue or present other issues associated with long term foreign body exposure. Consequently, when a CRM or other IMD needs replacement, the replacement surgery can become unduly complicated. Based on this, the present invention provides CRM pouches and other IMD made of a fully-resorbable material, i.e., biodegradable and resorbable polymers used in the present invention. Such a pouch serves the needs of patients and practitioners at the time of implantation as well as in the future if the need arises to remove the CRM or other IMD.

SUMMARY OF THE INVENTION

The pouches of the invention can be fashioned into various sizes and shapes to match the implanted pacemakers, pulse generators, other CRMs and other implantable devices.

As used herein, "pouch," "pouches," "pouch of the invention" and "pouches of the invention" means any pouch, bag, skin, shell, covering, or other receptacle formed from a biodegradable polymer or from a any fully resorbable polymer film and shaped to encapsulate, encase, surround, cover or hold, in whole or in substantial part, an implantable medical device. The pouches of the invention have openings to permit leads and tubes of the IMD to extend unhindered from the IMD though the opening of the pouch. The pouches may also have porosity to accommodate monopolar devices that require the IMD to be electrically grounded to the surrounding tissue. An IMD is substantially encapsulated, encased, surrounded or covered when the pouch can hold the device and at least 20%, 30%, 50%, 60%, 75%, 80%, 85%, 90%, 95% or 98% of the device is within the pouch or covered by the pouch.

The present invention relates to pouches, coverings and the like made from made from fully resorbable and biodegradable polymers which can be formed into films, molded, electrospun and shaped as desired into pouches, bags, coverings, skins, shells or other receptacle and the like. Pouches of the invention have one or more biodegradable polymers to impart or control drug elution of particular profiles or other temporary effects.

The polymer matrix of the fully resorbable pouches can comprise one or more drugs. Such drugs include, but are not limited to, antimicrobial agents, anti-fibrotic agents, anesthetics and anti-inflammatory agents as well as other classes of drugs, including biological agents such as proteins, growth inhibitors and the like.

The resorbable polymer matrices of the invention are capable of releasing one or more drugs into surrounding bodily tissue and proximal to the device such that the drug reduces or prevents implant- or surgery-related complications. For example, by including an anesthetic agent, such that the agent predictably seeps or elutes into the surrounding bodily tissue, bodily fluid, or systemic fluid, one has a useful way to attenuate the pain experienced at implantation site. In another example, replacing the anesthetic agent with an anti-inflammatory agent provides a way to reduce the swelling and inflammation associated implantation of the device and/or pouch. In yet another example, by delivering an antimicrobial agent in the same manner and at a therapeutically-effective dose, one has a way to provide a rate of drug release sufficient to prevent colonization of the pouch, the CRM or other IMD, and/or the surgical implantation site by bacteria for at least the period following surgery necessary for initial healing of the surgical incision.

Hence, the fully resorbable polymer pouches can be formed and shaped to encapsulate, encase or surround a pacemaker, a defibrillator or generator, an implantable access system, a neurostimulator, a drug delivery pump (e.g., intrathecal delivery system or a pain pump) or any other IMD for the purpose of securing those devices in position, providing pain relief, inhibiting scarring or fibrosis and/or for inhibiting bacterial growth on or in the tissue surrounding the device. Films are formed into an appropriate shape to hold the IMD.

In accordance with the invention, "fully resorbable polymer film" or "films" is used as a convenient reference to poured films, molded films, sheets, electrospun films, electrospun forms, any form, shape or film made by any other technique, no matter how those entities (i.e., "films") are made including by pre-forming a shape, injection molding, compression molding, dipping, spraying, electrospinning, thermoforming and the like. The fully resorbable polymer films are made from one or more fully resorbable, biodegradable polymers and are formed into a pouch, covering, skin, shell, receptacle, or other shape suitable for the IMD to encapsulate, encase or otherwise surround and hold, wholly or in substantial part, an IMD. Further, any of these films can be made porous, and the percentage to which they cover the IMD can be adjusted by punching holes, piercing the film (before or after shaping) or forming holes (see, e.g., FIGS. 3 and 4 below).

The pouches of the invention can deliver multiple drugs from one or more independent layers, some of which may contain no drug.

The invention thus provides a method of delivering drugs at controlled rates and for set durations of time using biodegradable, resorbable polymers.

DETAILED DESCRIPTION OF THE INVENTION

Figure 1:
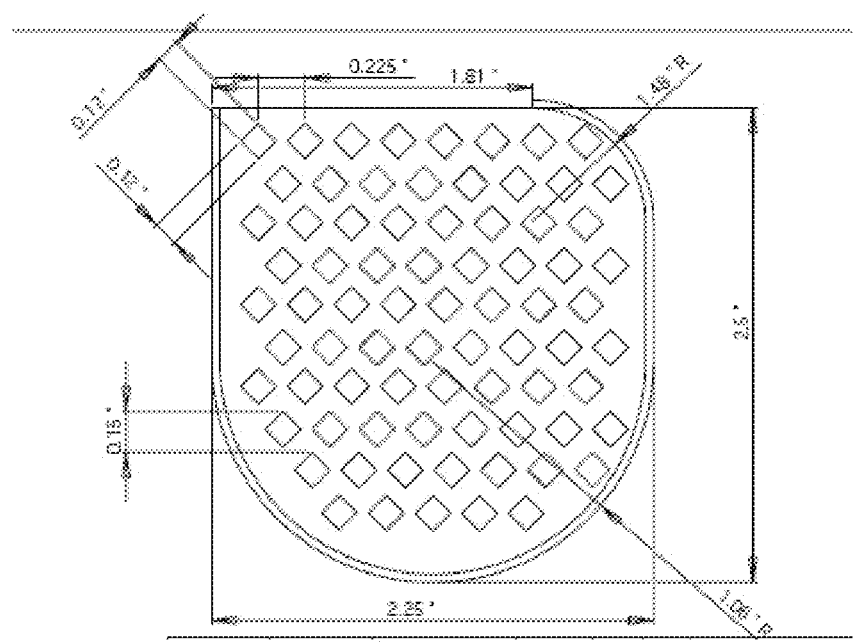
FIG. 1 is a schematic diagram of a fully resorbable CRM pouch.

The pouches of the invention comprise one or more biodegradable polymers, optionally in layers, and each layer independently further containing one or more drugs. The physical, mechanical, chemical, and resorption characteristics of the polymer enhance the clinical performance of the pouch and the surgeon's ability to implant a CRM or other IMD.

These characteristics are accomplished by choosing a suitable thickness for the pouch and one or more biodegradable polymer. It is preferred to use biodegradable polymers with a molecular weight between about 10,000 and about 200,000 Daltons. Such polymers degrade at rates that maintain sufficient mechanical and physical integrity over at least one 1 week at 37° C. in an aqueous environment.

Additionally, the biodegradable polymer has a chemical composition complementary to the drug so that the polymer layer can contain between 2-50% drug at room temperature. In one embodiment, the pouch releases drug for at least 2-3 days. Such release is preferred, for example, when the drug is an analgesic to aide in localized pain management at the surgical site.

To achieve an analgesic affect, the anesthetic and/or analgesic should be delivered to the injured tissue shortly after surgery or tissue injury. A drug or drugs for inclusion in the pouches of the invention include, but are not limited to analgesics, anti-inflammatory agents, anesthetics, antimicrobial agents, antifungal agents, NSAIDS, other biologics (including proteins and nucleic acids) and the like. Antimicrobial and antifungal agents can prevent the pouch, device, and/or the surrounding tissue from being colonized by bacteria. One or more drugs are incorporated into the polymer matrix that forms the pouches of the invention.

In another embodiment, the pouch coating comprises an anesthetic such that the anesthetic elutes from the implanted pouch to the surrounding tissue of the surgical site for between 1 and 10 days, which typically coincides with the period of acute surgical site pain. In another embodiment, delivery of an antimicrobial drug via a pouch of the invention can create an inhibition zone against bacterial growth and colonization surrounding the implant during the healing process (e.g., usually about 7-30 days or less) and/or prevent undue fibrotic responses.

Anesthetics that contain amines, such as lidocaine and bupivacaine, are hydrophobic and are difficult to load in sufficient amounts into the most commonly used plastics employed in the medical device industry, such as polypropylene and other non-resorbable thermoplastics. When in their hydrochloride salt form, anesthetics cannot be effectively loaded in significant concentration into such non-resorbable thermoplastics because of the mismatch in hydrophilicity of the two materials.

Using biodegradable polymers avoids the issue of drug solubility, impregnation or adherence in or to the underlying device by releasing relatively high, but local, concentrations of those drugs over extended periods of time. For example, by modulating the chemical composition of the biodegradable polymer, a clinically-efficacious amount of anesthetic drug can be incorporated into a pouch of the invention to assure sufficient drug elution and to provide surgical site, post-operative pain relief for the patient.

Other elution profiles, with faster or slower drug release over a different (longer or shorter) times, can be achieved by altering the thickness of the film or the layers that form the pouch, the amount of drug in the depot layer and the hydrophilicity of the biodegradable polymer.

Biodegradable Polymers

The pouches of the invention comprise one or more biodegradable polymers, and optionally contain one or more drugs. Methods of making biodegradable polymers are well known in the art. The biodegradable polymers suitable for use in the invention include but are not limited to:

polylactic acid, polyglycolic acid and copolymers and mixtures thereof such as poly(L-lactide) (PLLA), poly(D,L-lactide) (PLA);

polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL);

polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

In some embodiments, biodegradable polymers of the invention have diphenol monomer units that are copolymerized with an appropriate chemical moiety to form a polyarylate, a polycarbonate, a polyiminocarbonate, a polyphosphonate or any other polymer.

The preferred biodegradable polymers are tyrosine-based polyarylates including those described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337. These patents and publications also disclose other polymers containing tyrosine-derived diphenol monomer units or other diphenol monomer units, including polyarylates, polycarbonates, polyiminocarbonates, polythiocarbonates, polyphosphonates and polyethers.

Likewise, the foregoing patents and publications describe methods for making these polymers, some methods of which may be applicable to synthesizing other biodegradable polymers. Finally, the foregoing patents and publications also describe blends and copolymers with polyalkylene oxides, including polyethylene glycol (PEG). All such polymers are contemplated for use in the present invention.

The representative structures for the foregoing polymers are provide in the above-cited patents and publications which are incorporated herein by reference.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

Additional preferred polyarylates are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used in forming the polyarylates) include succinate, glutarate, adipate and glycolic acid.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate and DT PEG ester succinate.

In a preferred embodiment, the polyarylates are the DTE-DT succinate family of polymers, e.g., the P22-xx family of polymers having from 5-40% DT, including but not limited to, about 1, 2, 5, 10, 15, 20, 25, 27.5, 30, 35 and 40% DT.

Additionally, any of the foregoing polymers used in the present invention can have from 0.1-99.9% PEG diacid or any other polyalkylene oxide diacid, see e.g., U.S. provisional application Ser. No. 60/733,988, filed Nov. 3, 2005, its corresponding PCT application, filed Nov. 3, 2006 and U.S. Ser. No. 60/983,108, filed Oct. 26, 2007, each of which are incorporated herein by reference. Blends of polyarylates or other biodegradable polymers with polyarylates are also preferred.

The fully resorbable polymer pouches of the invention are prepared using any of the foregoing biodegradable polymers, and preferably using any one or more of the tyrosine-based polyarylates described above. Such polymers are dissolved in appropriate solvents to cast films, prepare spray coating solutions, electrospinning solutions, molding solutions and the like for forming a fully resorbable polymer film of the invention.

Fully resorbable pouches, as films, meshes, non-wovens and the like, can be created by several means: by spray coating a substrate, thermal or solvent casting, weaving, knitting or electrospinning, dip coating, extrusion, or molding. Sheets can be formed into a pouch configuration by thermoforming, or mechanical forming and heat setting, or adhesive, thermal or ultrasonic assembly. Pouches can be constructed directly from resorbable polymer by dip or spray coating a pre-formed shape, or injection or compression molding into the finished shape.

The biodegradable polymers can be formed into multi-layered fully resorbable polymer films, each layer containing the same or different polymers, the same or different drugs, and the same or different amounts of polymers or drugs. For example, a first film layer can contain drug, while the film layer coating layer contains either no drug or a lower concentration of drug. For example, a multilayer film can be made by casting a first layer, allowing it to dry, and casting a second or successive layer onto the first layer, allowing each layer to dry before casting the next layer.

Figure 4A:
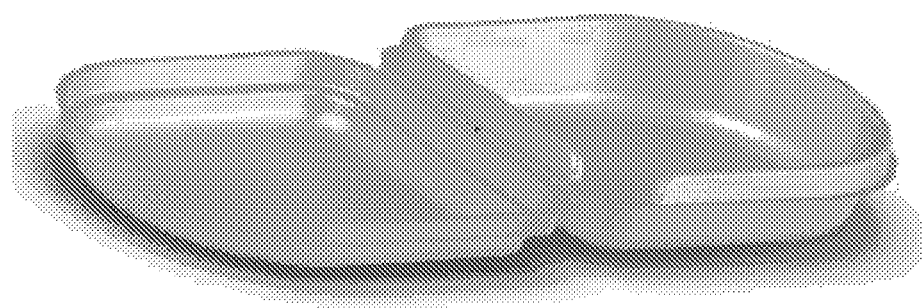
FIGS. 4A and 4B depicts two views of an aluminum mold used to form a resorbable clamshell-type pouch. The clamshell shape is designed to encase the IMD, has a ridge for folding (or can be easily folded over so that the sides interlock and the two halves fit snugly together. Additionally the clamshell has a space to allow the leads from the device to pass through the clamshell.
Figure 4B:
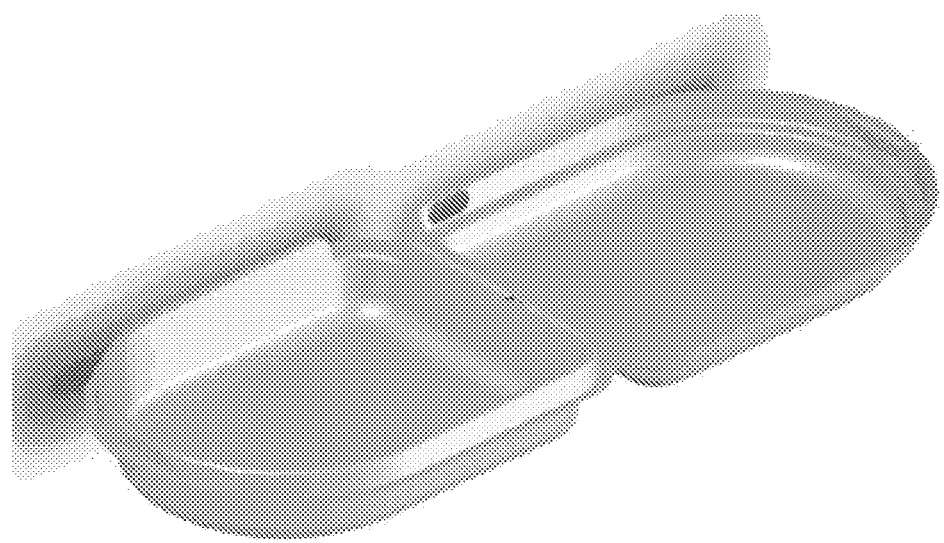

The pouches can be shaped to fit relatively snugly or more loosely around an IMD. For example, the clamshell shaped pouch shown in FIGS. 3 and 4 is designed to encase the IMD, is capable of being folded, and each half interlocks with the other half to secure the shell around the device and hold the device within the clamshell. Additionally, the clamshell has a space or opening sufficient to allow the leads from the device to pass through the clamshell. The number of spaces or opening in the pouch that are provided can match the number and placement of the leads or other tubes extending from the CRM or other IMD, as applicable for the relevant device. The pouches are constructed with polymers from the group described herein that are selected to have elastomeric properties if is desirable to have a pouch that fits tightly over the IMD.

The films can be laser cut to produce the desired shaped and sized pouches, coverings and the like. Two pieces can be sealed, by heat, by ultrasound or other method known in the art, leaving one side open to permit insertion of the device at the time of the surgical procedure.

In preferred embodiments, the shape and size of the pouch of the invention is similar to that of the DRM or IMD with which it is being used, and the pouch as a sufficient number of openings or spaces to accommodate the leads or tubings of the particular CRM or other IMD.

Figure 2:
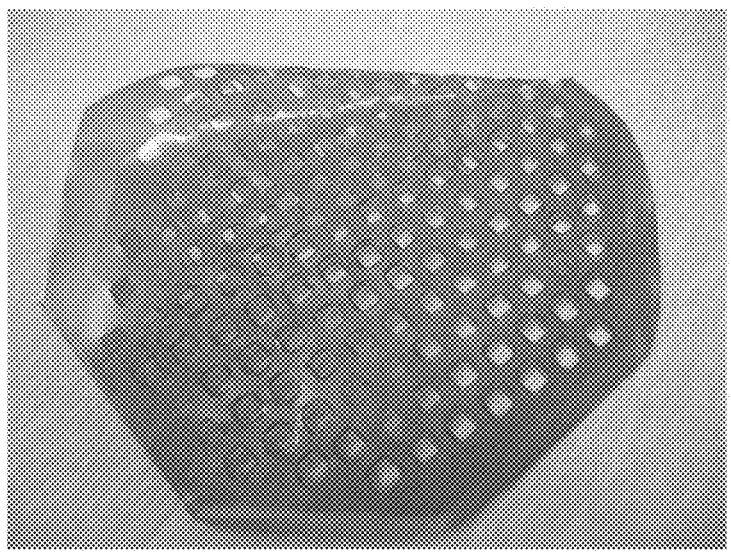
FIG. 2 is a picture of a fully resorbable CRM pouch, wherein the polymer matrix contains antimicrobial agents.
Figure 3A:
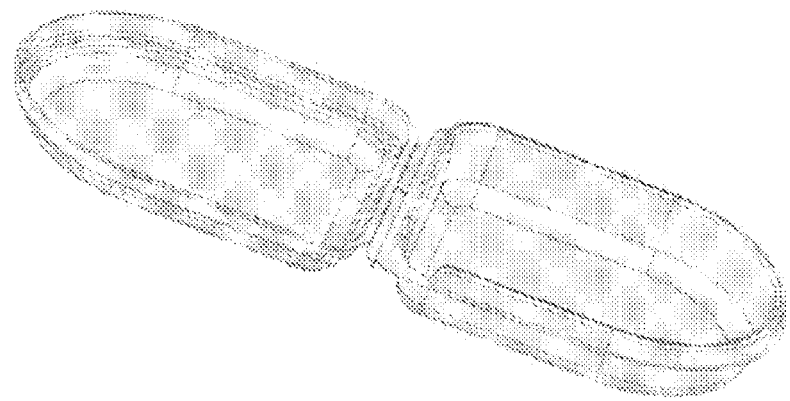
FIGS. 3A and 3B is a drawing of a resorbable clamshell-type pouch sized for a neurostimulator device, showing top, bottom and side views thereof.
Figure 3A:
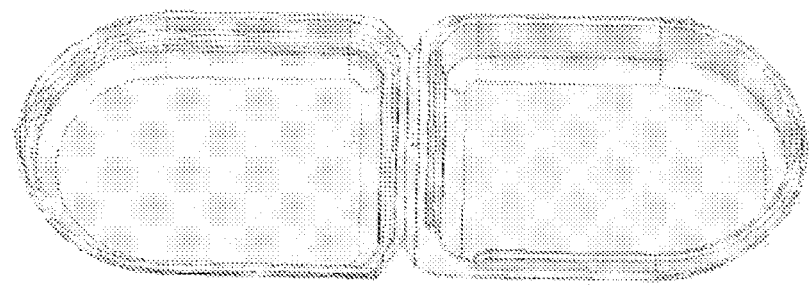
Figure 3A:
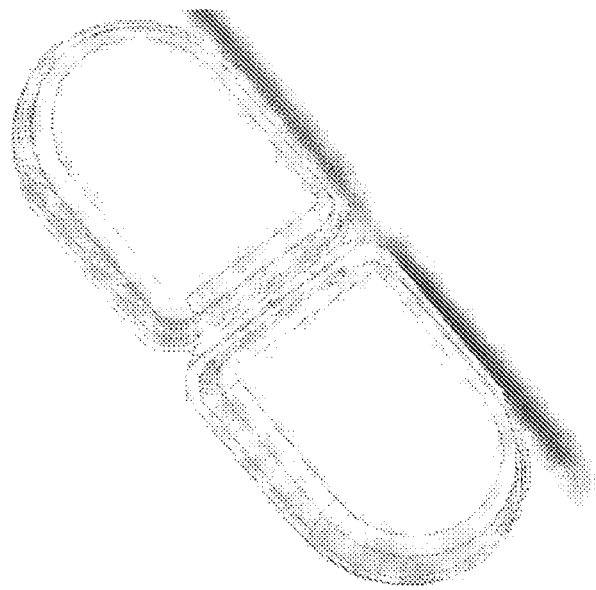
Figure 3B:
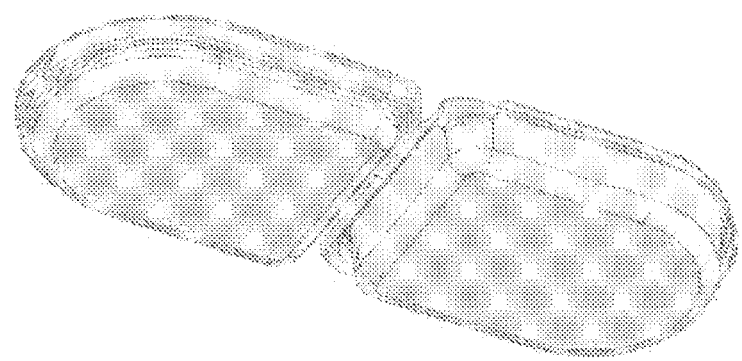
Figure 3B:
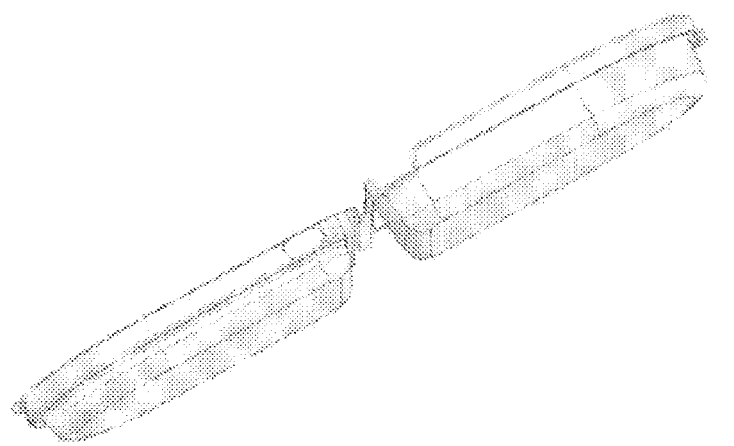
Figure 3B:
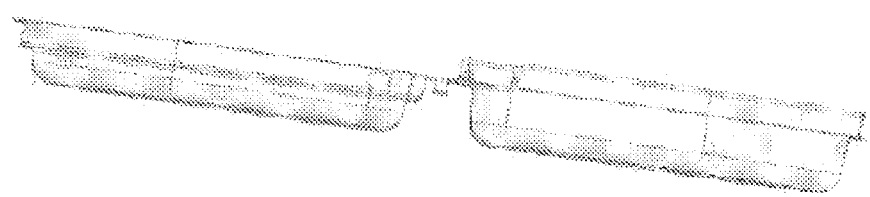

The pouches of the invention can be porous. As shown in FIGS. 1 and 2, porous pouches can be formed by punching holes or laser cutting holes in the films that form the pouch. Porous pouches can also by forming woven or non-woven fibers made from the biodegradable polymers into pouches. Depending on the fibers and the weave, such pouches may be microporous. As an example, the pouch need not completely encase or surround the IMD. An IMD is thus substantially encapsulated, encased, surrounded or covered when the pouch can hold the device and at least 20%, 30%, 50%, 60%, 75%, 80%, 85%, 90%, 95% or 98% of the device is within the pouch. Porous pouches and partially encased pouches permit contact with tissue and body fluids and are particularly useful with monopole CRM or other IMD devices. Porosity will contribute to the percentage of the IMD covered by the pouch. That is, an IMD is considered to be 50% covered if it is completely surrounded by a pouch that is constructed of a film with 50% voids or holes.

Drugs

Any drug, biological agent or active ingredient compatible with the process of preparing the pouches of the invention can be incorporated into the pouch or into one or more layers of the biodegradable polymer layers that form a pouch of the invention. Doses of such drugs and agents are known in the art. Those of skill in the art can readily determine the amount of a particular drug to include in the Pouches of the invention.

Examples of drugs suitable for use with the present invention include anesthetics, antibiotics (antimicrobials), anti-inflammatory agents, fibrosis-inhibiting agents, anti-scarring agents, leukotriene inhibitors/antagonists, cell growth inhibitors and the like. As used herein, "drugs" is used to include all types of therapeutic agents, whether small molecules or large molecules such as proteins, nucleic acids and the like. The drugs of the invention can be used alone or in combination.

Any pharmaceutically acceptable form of the drugs of the present invention can be employed in the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antimicrobials include, but are not limited to, triclosan, chlorhexidine, rifampin, minocycline (or other tetracycline derivative), vancomycin, gentamycin, cephalosporins and the like. In preferred embodiments the coatings contain rifampin and another antimicrobial agent, especially a tetracycline derivative. In another preferred embodiment, the coatings contains a cephalosporin and another antimicrobial agent. Preferred combinations include rifampin and minocycline, rifampin and gentamycin, and rifampin and minocycline.

Further antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin.

Examples of antifungals include amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Other drugs that can be incorporated into the coatings on the mesh pouches of the invention include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-flurouracil and the like.

Additional, drugs include those that act as angiogenensis inhibitors or inhibit cell growth such as epidermal growth factor, PDGF, VEGF, FGF (fibroblast growth factor) and the like. These drugs include anti-growth factor antibodies (neutrophilin-1), growth factor receptor-specific inhibitors such as endostatin and thalidomide.

Examples of anti-inflammatory compound include, but are not limited to, anecortive acetate; tetrahydrocortisol, 4,9(11)-pregnadien-17.alpha.,21-diol-3,20-dione and its -21-acetate salt; 11-epicortisol; 17.alpha.-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

Another useful drug that can be incorporated into the coatings of the invention is sodium 2-mercaptoethane sulfonate (Mesna). Mesna has been shown to diminish myofibroblast formation in animal studies of capsular contracture with breast implants [Ajmal et al. (2003) Plast. Reconstr. Surg. 112:1455-1461] and may thus act as an anti-fibrosis agent.

CRMs and Other IMDs

The CRMs and other IMDs used with the pouches of the invention include but are not limited to pacemakers, defibrillators, implantable access systems, neurostimulators, other stimulation devices, ventricular assist devices, infusion pumps or other implantable devices (or implantable components thereof) for delivering medication, hydrating solutions or other fluids, intrathecal delivery systems, pain pumps, or any other implantable system to provide drugs or electrical stimulation to a body part.

Implantable cardiac rhythm management devices (CRMs) are a form of IMDs and are life-long medical device implants. CRMs ensure the heart continually beats at a steady rate. There are two main types of CRM devices: implantable cardiac rhythm management devices and implantable defibrillators.

The ICDs, or implantable cardioverter defibrillator, and pacemakers share common elements. They are permanent implants inserted through relatively minor surgical procedures. Each has 2 basic components: a generator and a lead. The generator is usually placed in a subcutaneous pocket below the skin of the breastbone and the lead is threaded down and into the heart muscle or ventricle. The common elements of placement and design result in shared morbidities, including lead extrusion, lead-tip fibrosis, and infection. Although infection rates are purportedly quite low, infection is a serious problem as any bacterial contamination of the lead, generator, or surgical site can travel directly to the heart via bacterial spreading along the generator and leads. Endocarditis, or an infection of the heart, has reported mortality rates as high as 33%.

An ICD is an electronic device that constantly monitors heart rate and rhythm. When it detects a fast, abnormal heart rhythm, it delivers energy to the heart muscle. This action causes the heart to beat in a normal rhythm again in an attempt to return it to a sinus rhythm.

The ICD has two parts: the lead(s) and a pulse generator. The lead(s) monitor the heart rhythm and deliver energy used for pacing and/or defibrillation (see below for definitions). The lead(s) are directly connected to the heart and the generator. The generator houses the battery and a tiny computer. Energy is stored in the battery until it is needed. The computer receives information on cardiac function via the leads and reacts to that information on the basis of its programming.

The different types of ICDs include, but are not limited to, single chamber ICDs in which a lead is attached in the right ventricle. If needed, energy is delivered to the ventricle to help it contract normally; dual chamber ICDs in which the leads are attached in the right atrium and the right ventricle. Energy is delivered first to the right atrium and then to the right ventricle to ensure that the heart beats in a normal sequence; and biventricular ICDs in which leads are attached in the right atrium, the right ventricle and the left ventricle. This arrangement helps the heart beat in a more balanced way and is specifically used for patients with heart failure.

A pacemaker is a small device that sends electrical impulses to the heart muscle to maintain a suitable heart rate and rhythm. A pacemaker can also be used to treat fainting spells (syncope), congestive heart failure, and hypertrophic cardiomyopathy. Pacemakers are generally implanted under the skin of the chest during a minor surgical procedure. The pacemaker is also comprised of leads and a battery-driven pulse generator. The pulse generator resides under the skin of the chest. The leads are wires that are threaded through the veins into the heart and implanted into the heart muscle. They send impulses from the pulse generator to the heart muscle, as well as sense the heart's electrical activity.

Each impulse causes the heart to contract. The pacemaker may have one to three leads, depending on the type of pacemaker needed to treat your heart problem.

The different types of pacemakers include, but are not limited to single chamber pacemakers which use one lead in the upper chambers (atria) or lower chambers (ventricles) of the heart; dual chamber pacemakers which use one lead in the atria and one lead in the ventricles of your heart; and biventricular pacemakers which use three leads: one placed in the right atrium, one placed in the right ventricle, and one placed in the left ventricle (via the coronary sinus vein).

The pouches of the invention can thus be designed to fit a wide range of pacemakers and implantable defibrillators from a variety of manufacturers (see Table 1). Sizes of the CRMs vary and typically size ranges are listed in Table 1.

TABLE 1

CRM Devices

| Manufacturer | Device | Type | Model | Size (H" × L" × W") |
|---|---|---|---|---|
| Medtronic | EnPulse Pacing system | Pacing system | E2DR01 | 1.75 × 2 × 0.33 |
| Medtronic | EnPulse Pacing system | Pacing system | E2DR21 | 1.75 × 1.63 × 0.33 |
| Medtronic | EnRhythm Pacing system | Pacing system | P1501DR | 1.77 × 2 × 0.31 |
| Medtronic | AT500 Pacing system | Pacing system | AT501 | 1.75 × 2.38 × 0.33 |
| Medtronic | Kappa DR900 & 700 series | Pacing system | DR900, DR700 | 1.75-2 × 1.75-2 × 0.33 |
| Medtronic | Kappa DR900 & 700 series | Pacing system | SR900, SR700 | 1.5-1.75 × 1.75-2 × 0.33 |
| Medtronic | Sigma | Pacing system | D300, D200, D303, D203 | 1.75 × 2 × 0.33 |
| Medtronic | Sigma | Pacing system | DR300, DR200, DR303, DR306, DR203 | 1.75-2 × 2 × 0.33 |
| Medtronic | Sigma | Pacing system | VDD300, VDD303 | 1.75 × 1.75 × 0.33 |
| Medtronic | Sigma | Pacing system | S300, S200, S100, S303, S203, S103, S106, VVI-103 | 1.63 × 2 × 0.33 |
| Medtronic | Sigma SR | Pacing system | SR300, S200, SR303, SR306, SR203 | 1.63 × 2 × 0.33 |
| Medtronic | Entrust | Defibrillator | D154VRC 35J | 2.44 × 2 × 0.6 |
| Medtronic | Maximo & Marquis family | Defibrillator | | Size of a pager |
| Medtronic | Gem family | Defibrillator | III T, III R, III R, II R, II VR | Size of a pager |
| Guidant | Contak Renewal TR | Pacing system | H120, H125 | 2.13 × 1.77 × 033 |
| St. Jude | Identity | Pacing system | ADx DR, ADx SR, ADx XL, ADx VDR | 1.6-1.73 × 1.73-2.05 × 0.24 |
| St. Jude | Integrity | Pacing system | ADx DR, ADx SR | 1.6-1.73 × 1.73-2.05 × 0.24 |

Implantable neurostimulators are similar to pacemakers in that the devices generate electrical impulses. These devices send electrical signals via leads to the spine and brain to treat pain and other neurological disorders. For example, when the leads are implanted in the spine, the neurostimulation can be used to treat chronic pain (especially back and spinal pain); when the leads are implanted in the brain, the neurostimulation can be used to treat epilepsy and essential tremor including the tremors associated with Parkinson's disease and other neurological disorders. Neurostimulation can be used to treat severe, chronic nausea and vomiting as well as urological disorders. For the former, electrical impulses are sent to the stomach; for the latter, the electrical impulses are sent to the sacral nerves in the lower back. The implant location of the neurostimulator varies by application but, in all cases, is placed under the skin and is susceptible to infection at the time of implantation and pos-implantation. Likewise, reintervention and replacement of batteries in the neurostimulators can occur at regular intervals.

The pouches of the invention can thus be designed to fit a wide range of neurostimulators from a variety of manufacturers (see Table 2). Sizes of the neurostimulators vary and typically size ranges are listed in Table 2.

TABLE 2

Neurostimulators

| Manufacturer | Device | Type | Model | Size (H" × L" × W") |
|---|---|---|---|---|
| Medtronic | InterStim INS | Neurostimulation | 3023 | 2.17 × 2.4 × 0.39 |
| Medtronic | InterStim INS II | Neurostimulation | 3058 | 1.7 × 2.0 × 0.3 |
| Medtronic | RESTORE | Neurostimulation | 37711 | 2.56 × 1.93 × 0.6 |
| Advanced Bionics (Boston Scientific) | Precision IPG | Neurostimulation/Spinal Cord Stimulator | | 2.09 × 1.70 × 0.35 |
| Cyberonics | VNS Therapy system | Neurostimulation/Epilepsy | 102 | 2.03 × 2.06 × 0.27 |
| Cyberonics | VNS Therapy system | Neurostimulation/Epilepsy | 102R | 2.03 × 2.32 × 0.27 |
| ANS (St. Jude) | Eon | Neurostimulation | | Comparable to Medtronic Restore |
| ANS (St. Jude) | Genesis RC | Neurostimulation | | Comparable to Medtronic Restore |
| ANS (St. Jude) | Genesis XP | Neurostimulation | | Comparable to Medtronic Restore |

Reported infection rates for first implantation are usually quite low (less than 1%); however, they increase dramatically when a reintervention is necessary. Reintervention often requires the removal of the generator portion of the ICD, pacemaker, neurostimulator, drug pump or other IMD and having a resorbable pouch enhances that process.

Other IMDs for use in the invention are drug pumps, especially pain pumps and intrathecal delivery systems. These devices generally consist of an implantable drug pump and a catheter for dispensing the drug. The implantable drug pump is similar in size to the neurostimulators and CRMs. Further implantable medical devices include, but are not limited to, implantable EGM monitors, implantable access systems, or any other implantable system that utilizes battery power to provide drugs or electrical stimulation to a body part.

Antimicrobial Efficacy

Antimicrobial efficacy of the pouches of the invention can be demonstrated in laboratory (in vitro), for example, using the modified Kirby-Bauer Antibiotic Susceptibility Test (Disk Diffusion Test) (in vitro) to assess bacterial zones of inhibitions or by the Anti-microbial Finishes Method to access the reduction in bacteria achieved with the pouch (in vitro). In such experiments, a small disk of the pouch is cut and used. Antimicrobial efficacy can also be demonstrated in vivo using animal models of infection. For example, a pouch and device combination are implanted in an animal, the surgical site is deliberately infected with a predetermined level of a pathogenic microorganism, such as *Staphylococcus aureus* or *Staphylococcus epidermis*, and the animal is monitored for signs of infection and inflammation. At sacrifice, the animal is assessed for inflammation, fibrosis and bacterial colonization of the pouch (to the extent still present), device and the surrounding tissues.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference.

Example 1

Resorbable Pouch

To prepare a resorbable pouch, 18.0 g of polymer, 1.0 g minocycline and 1.0 g rifampin are dissolved in 75 mL of a solution of tetrahydrofuran-methanol. This solution is poured over a level non-stick Teflon surface. A calibrated stainless steel gardner knife is used to spread the solution to the desired thickness, typically to a range of from about 2 and about 400 microns.

The film is dried at ambient temperature overnight. Thereafter, the solvent cast film is dried in a convection oven at 50° C. for 1 day, the temperature of the oven is increased to 80° C. and the film is dried further for 2 days. At this point, the dried film is ready for laser cutting and further processing to create the pouch, i.e., cutting and sealing three of the sides. The pouch is cut for overall shape to match the desired CRM and to create a mesh like covering. A CRM pouch made using a DT-DTE succinate polymer is shown in FIG. 4.

Example 2

Resorbable Clamshell Pouch

To prepare a resorbable clamshell pouch, a film is prepared as described above in Example 1. After the film is dried, it is thermoformed into the clamshell shape by placing a film sheet into a frame and heating the film to about 90-100° C. and lowering the frame over a clamshell-shaped mold as shown in FIG. 7 whereby the film takes the shape of the clamshell mold. The molded clamshell is cooled, freed from the mold, and laser cut from the film sheet.

REFERENCES

1. Hospital Infections Program, National Centrer for Infectious Disease, CDC. Public health focus: surveillance, prevention, and control of nosocomial infections. MMWR Weekly, 1992; 41:783-7.
2. Perencevich E N, Sands K E, Cosgrove S E, et. al. Health and economic impact of surgical site infections diagnosed after hospital discharge. Emerging Infect Dis, 2003; 9:196-203.
3. Baddour L M, Bettmenn M A, Bolger A F, et. al. Nonvalvular cardiovascular device-related infections. Circulation, 2003; 108:2015-31.
4. Darouiche R O, Treatment of infections associated with surgical implants. NEJM, 2004; 350:1422-9.
5. Meakins J L, Prevention of Postoperative Infection. In ACS Surgery: Principals and Practice. American College of Surgeons, 2005.
6. Hambraeus A, Bengtsson S, Laurell G. Bacterial contamination in a modern operating suite, 2. effect of a zoning system on contamination of floors and other surfaces. J Hyg, 1978; 80:57-67.
7. Da Costa A, Kirkorian G, Cucherat M, et. al. Antibiotic prophylaxis for permanent pacemaker implantation: a meta-analysis. Circulation, 1998; 97:1796-1801.
8. Darouiche R O, Antimicrobial approaches for preventing infections associated with surgical implants. Clin Infect Dis 2003; 36:1284-9.
9. Pearson M L and Abrutyn E, Reducing the risk for catheter-related infections: a new strategy. Ann Intern Med, 1997; 127:304-6.
10. Donlon R M, Biofilms and device-associated infections. Emerg Infect Dis, 2001; 7:277-81.
11. Maki D G and Tambyah P A, Engineering out the risk of infection with urinary catheters. Emerg Infect Dis, 2001; 7:342-7.
12. Maki D G, Stolz S M, Wheeler S and Mermel L A. Prevention of central venous catheter-related blood stream infection by use of an antiseptic-impregnated catheter: a randomized, controlled trial. Ann Intern Med, 1997;127:257-66.
13. Raad I, Darouiche R, Dupuis J, et. al., Central venous catheters coated with minocycline and rifampin for the prevention of catheter-related colonization and bloodstream infections: a randomized, double-blind trial. Ann Intern Med, 1997; 127:267-74.
14. Collin G R, Decreasing catheter colonization through the use of an antiseptic-impregnated catheter: a continuous quality improvement project. Chest, 1999; 115:1632-40.
15. Tennenberg S, Lieser M, McCurdy B, Boomer G, Howington E, Newman C, Wolf I A prospective randomized trial of an antibiotic- and antiseptic-coated central venous catheter in the prevention of catheter-related infections. Arch Surg, 1997; 132:1348-51
16. George S J, Vuddamalay P, Boscoe M J. Antiseptic-impregnated central venous catheters reduce the incidence of bacterial colonization and associated infection in immunocompromised transplant patients. Eur J Anaesthesiol, 1997; 14:428-31.
17. Segura M, Alvarez-Lerma F, Tellado J M, Jimenez-Ferreres J, Oms L, Rello J, Baro T, Sanchez R, Morera A, Mariscal D, Marrugat J, Sitges-Serra A. A clinical trial on the prevention of catheter-related sepsis using a new hub model. Ann Surg, 1996; 223:363-9.
18. Bach A, Schmidt H, Bottiger B, Schreiber B, Bohrer H, Motsch J, Martin E, Sonntag H G. Retention of antibacterial activity and bacterial colonization of antiseptic-bonded central venous catheters. J Antimicrob Chemother, 1996; 37:315-22.
19. Li H, Fairfax M R, Dubocq F, et. al. Antibacterial activity of antibiotic coated silicon grafts. J Urol, 1998; 160: 1910-3.
20. Darouiche R O, Mansouri N D, Raad H. Efficacy of antimicrobial-impregnated silicone sections from penile implants in preventing device colonization in an animal model. Urology, 2002; 59:303-7.
21. Darouiche R O, Meade R, Mansouri N D, Netscher D T. In vivo efficacy of antimicrobial-impregnated saline-filled silicone implants. Plast Reconstr Surg, 2002; 109:1352-7.
22. Chamis A L, Peterson G E, Cabell C H, et. al. *Staphylococcus aureus* bacteremia in patients with permanent pacemakers of implantable cardioverter-defribrillators. Circulation, 2001; 104:1029-33.

We claim:

1. A kit comprising:
   an implantable medical device unit; and
   a resorbable pouch comprising a biodegradable and resorbable polymer formed to at least partially enclose or encase said implantable medical device unit and one or more drugs,
   wherein said pouch is a thermoformed clamshell type pouch having a first half and a second half connected by a hinge.

2. The kit of claim 1, wherein said medical device unit is a cardiac rhythm management device.

3. The kit of claim 1, wherein said medical device unit is a pacemaker, a defibrillator, a pulse generator, an implantable access system, a drug pump or a neurostimulator.

4. The kit of claim 1, wherein said biodegradable and resorbable polymer is selected from the group consisting of a polylactic acid, polyglycolic acid, poly(L-lactide), poly(D, L-lactide), polyglycolic acid, poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polyethylene oxide, polyoxaester, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, poly(phosphazene), poly(phosphate ester), poly(amino acid), polydepsipeptide, maleic anhydride copolymer, polyiminocarbonates, poly [(97.5% dimethyl-trimethylene carbonate)-co-(2.5% trimethylene carbonate)], poly(orthoesters), tyrosine-derived polyarylate, tyrosine-derived polycarbonate, tyrosine-derived polyiminocarbonate, tyrosine-derived polyphosphonate, polyalkylene oxide, hydroxypropylmethylcellulose, polysaccharide, protein, and copolymers, terpolymers and blends of any thereof.

5. The kit of claim 1, wherein said biodegradable and resorbable polymer comprises one or more tyrosine-derived diphenol monomer units.

6. The kit of claim 1, wherein said one or more drugs are selected from the group consisting of antimicrobial agents, anesthetics, analgesics, anti-inflammatory agents, anti-scarring agents, anti-fibrotic agents and leukotriene inhibitors.

7. The kit of claim 1, wherein said one or more drugs is an anesthetic.

8. The kit of claim 1, wherein said one or more drugs is an antimicrobial agent.

9. The kit of claim 8, wherein said antimicrobial agent is selected from the group consisting of rifampin, minocycline, silver/chlorhexidine, vancomycin, a cephalosporin, gentamycin, triclosan and combinations thereof.

10. The kit of claim 8, wherein said antimicrobial agent is two antimicrobial agents, said agents being rifampin and a tetracycline derivative.

11. The kit of claim 1, wherein said pouch is configured to permit ingrowth of tissue into said pouch to resist post implantation migration of said implantable medical device unit.

12. The kit of claim 1, wherein said pouch has a porosity sufficient to electrically ground said implantable medical device unit to tissue surrounding said pouch.

13. The kit of claim 1, wherein said pouch is configured to removably enclose or encase said implantable medical device unit.

14. The kit of claim 1, wherein said implantable medical device unit is movable within said pouch prior to implantation of said pouch and is fixed relative to said pouch following implantation of said pouch.

15. The kit of claim 1, wherein said pouch is woven or knit from resorbable fibers, or made from electrospun resorbable fibers.

16. The kit of claim 1, wherein said biodegradable and resorbable polymer has a molecular weight between about 10,000 and about 20,000 Daltons.

17. The kit of claim 1, wherein said biodegradable and resorbable polymer is a member of the P22-xx family.

18. The kit of claim 1, wherein said biodegradable and resorbable polymer has elastomeric characteristics such that said pouch fits tightly over said implantable medical device unit.

19. A kit comprising:
an implantable medical device unit; and
a resorbable pouch comprising a biodegradable and resorbable polymer formed to at least partially enclose or encase said implantable medical device unit and one or more drugs,
wherein said pouch is a thermoformed clamshell type pouch having a first half and a second half connected by a hinge, and
wherein said biodegradable and resorbable polymer is a member of the P22-xx family having from 5-40% desaminotyrosyl-tyrosine.

20. A kit comprising:
an implantable medical device unit; and
a resorbable pouch comprising a biodegradable and resorbable polymer formed to at least partially enclose or encase said implantable medical device unit and one or more drugs,
wherein said pouch is a thermoformed clamshell type pouch having a first half and a second half connected by a hinge, and
wherein said biodegradable and resorbable polymer is a member of the P22-xx family having from 27.5% desaminotyrosyl-tyrosine.

* * * * *